US008535527B2

(12) United States Patent  
Irgum

(10) Patent No.: US 8,535,527 B2  
(45) Date of Patent: Sep. 17, 2013

(54) MONOLITHIC SUPPORTS AND METHODS FOR THEIR PRODUCTION

(75) Inventor: Knut Irgum, Bullmark (SE)

(73) Assignee: Merck Patent GmbH, Darmstadt (DE)

( * ) Notice: Subject to any disclaimer, the term of this patent is extended or adjusted under 35 U.S.C. 154(b) by 348 days.

(21) Appl. No.: 12/918,173

(22) PCT Filed: Jan. 27, 2009

(86) PCT No.: PCT/EP2009/000494  
§ 371 (c)(1),  
(2), (4) Date: Aug. 18, 2010

(87) PCT Pub. No.: WO2009/103399  
PCT Pub. Date: Aug. 27, 2009

(65) Prior Publication Data  
US 2010/0326919 A1 Dec. 30, 2010

Related U.S. Application Data

(60) Provisional application No. 61/029,582, filed on Feb. 19, 2008.

(30) Foreign Application Priority Data

Feb. 19, 2008 (SE) ...................................... 0800375

(51) Int. Cl.  
*B01D 15/00* (2006.01)  
*B01D 15/08* (2006.01)  
*B29C 67/00* (2006.01)  
*C02F 1/28* (2006.01)

(52) U.S. Cl.  
USPC .......... 210/198.1; 210/635; 210/656; 264/41; 264/214

(58) Field of Classification Search  
USPC .................... 210/198.2, 656, 500.38, 500.42, 210/321.75, 635; 530/417, 412, 918; 427/244; 436/161; 264/41, 512, 214  
See application file for complete search history.

(56) References Cited

U.S. PATENT DOCUMENTS

| 3,427,277 | A |   | 2/1969  | Davis |
|-----------|---|---|---------|-------|
| 4,340,479 | A | * | 7/1982  | Pall ............................... 210/490 |
| 5,053,133 | A | * | 10/1991 | Klein et al. .............. 210/500.38 |
| 5,277,811 | A |   | 1/1994  | Moya |
| 5,695,640 | A | * | 12/1997 | Tseng ..................... 210/500.38 |
| 5,929,214 | A | * | 7/1999  | Peters et al. ................. 530/417 |
| 6,036,726 | A |   | 3/2000  | Yang et al. |

(Continued)

FOREIGN PATENT DOCUMENTS

| WO | WO 01/83072 A1 | 11/2001 |
| WO | WO 01/94457 A2 | 12/2001 |
| WO | WO 02/40130 A1 | 5/2002 |

OTHER PUBLICATIONS

International Search Report of PCT/EP2009/000494 (Oct. 8, 2009).

(Continued)

*Primary Examiner* — Ana Fortuna  
(74) *Attorney, Agent, or Firm* — Millen, White, Zelano & Branigan, P.C.

(57) ABSTRACT

The present invention provides monolithic supports produced from linear aliphatic polyamides. It also provides a method of producing said monolithic supports by dissolution/precipitation of linear aliphatic polyamides. Finally, the invention provides using said supports in chromatography as well as chromatography columns containing said supports.

13 Claims, 6 Drawing Sheets

(56) References Cited

U.S. PATENT DOCUMENTS

Figure 1:
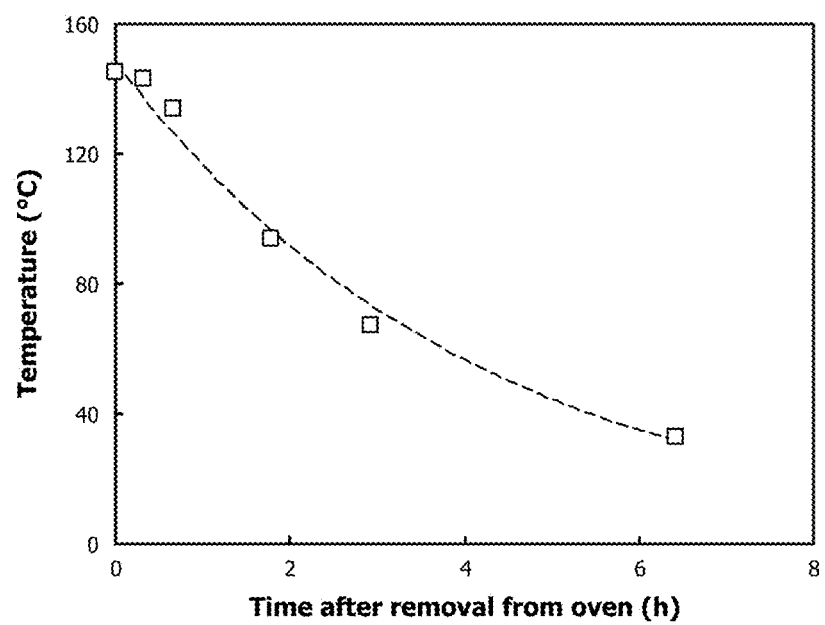

| | | | |
|---|---|---|---|
| 8,217,094 B2* | 7/2012 | Hosoya et al. | 521/178 |
| 2002/0037939 A1 | 3/2002 | McKinnon | |
| 2003/0029802 A1 | 2/2003 | Ruiz | |
| 2003/0071383 A1 | 4/2003 | Ma | |
| 2004/0138432 A1* | 7/2004 | Viklund et al. | 530/417 |
| 2008/0152865 A1* | 6/2008 | Takeno et al. | 428/134 |
| 2010/0038298 A1* | 2/2010 | Angelini et al. | 210/198.2 |
| 2010/0326919 A1* | 12/2010 | Irgum | 210/656 |

OTHER PUBLICATIONS

C.N. Kartalis et al., "Pure Component Recovery from Polyamide 6/6 6 Mixtures by Selective Dissolution and Reprecipitation", Journal of Applied Polymer Science, vol. 86 (2002) pp. 1924-1930.

F. Svec et al., "Design of the Monolithic Polymers Used in Capillary Electrochromatography Columns", Journal of Chromatography A, vol. 887 (2000) pp. 3-29.

* cited by examiner

MONOLITHIC SUPPORTS AND METHODS FOR THEIR PRODUCTION

This application claims the benefit of the filing date of U.S. Provisional Application Ser. No. 61/029,582 filed Feb. 19, 2008, which is incorporated by reference herein.

The present invention provides monolithic supports produced from linear aliphatic polyamides. It also provides a method of producing said monolithic supports by dissolution/precipitation of linear aliphatic polyamides. Finally, the invention provides using said supports in chromatography as well as chromatography columns containing said supports.

TECHNICAL BACKGROUND

Porous monolithic structures have evolved into versatile carrier materials in a wide range of flow-through applications in chemical analysis, biosciences, catalysis, etc. (Svec et al., eds. "Monolithic materials", ISBN-13:978-0-444-50879-9, Elsevier 2003) Such organic monoliths are almost invariably made by direct mould polymerization of precursor monomers (commonly vinylic, but more recently also epoxy-based condensation systems) in the presence of porogens, which establish flow-through and diffusive pores in the material. Direct polymerization in situ is simple and has many advantages, but also drawbacks such as difficulties in establishing a spatially homogenous pore size distribution due to thermal gradients caused by exothermic polymerization reactions, since the pore formation mechanism is highly sensitive to the polymerization temperature. The decrease in specific volume when monomers are converted to polymers also causes shrinkage and related strain, which can explain structural breakdown or detachment from the mould walls, as often seen in monoliths directly polymerized from vinylic monomers. The primary object when preparing a monolith for separation purposes is to establish a pore system with evenly spaced equi-sized pores. In conventional direct monolith polymerizations, this pore formation is effected by the non-polymerizable porogens, which are selected to be a good solvent for the monomer but an intermediate to bad solvent for the polymer formed.

Accordingly, there is a need for an improved method for producing porous monolithic structures that does not have the drawbacks mentioned above.

Numerous polymers can be brought into solutions by solvents, and the parameters that determine the swelling and eventual dissolution is the solvent quality and $\Theta$-temperature in the polymer/solvent system in question. Dissolution/precipitation is a technique often used for preparing membranes, where one face of the cast polymer solution is open to the further treatment (evaporation, solvent treatment, etc.). The means most often used for controlling the polymer precipitation rate (establishing deviation from $\Theta$-conditions) is selective vaporization or treatment with a non-solvent, used as a liquid bath or deposited onto the membrane from the gas phase.

Polyamide is among the polymers that have found widest uses as membranes prepared by dissolution/precipitation and the applications span the environmental, biotechnological, and medical sciences. Examples of such applications are in desalination by reverse osmosis (Shibata et al., Journal of Applied Polymer Sciences 2000, 75, 1546-1553), waste water treatment (Sheriff et al., J. Agric. Food Chem. 2002, 50, 2802-2811), affinity chromatography for protein purification (Castilho et al., Journal of Membrane Science 2000, 172, 269-277; Castilho et al., Journal of Membrane Science 2002, 207, 253-264; Beeskow et al., Journal of Colloid and Interface Sciences 1997, 196, 278-291), microfiltration (Persson et al., Journal of Membrane Science 2003, 223, 11-21; Yang et al., Chem. Eng. Technol. 2006, 29, 631-636; Gholap et al., Journal of Membrane Science 2001, 183, 89-99), and hemodialysis (Mochizuki et al., Journal of Applied Polymer Sciences 1997, 65, 1713-1721). The popularity of polyamide membranes is a result of material durability, wide range of hydrophilic-hydrophobic (amphiphilic) properties and numerous possibilities for functionalization. Introduction of surface functional groups can be made by chemical conversion or by thermal and photo-induced (Teke et al., Process Biochemistry 2006; Wu et al., Journal of Membrane Science 2006, 283, 13-20; Eldin et al., Advances in Polymer Technology 1999, 18, 109-123) grafting, and modifications that target the main chain amide groups (Jia et al., Polymer 2006, 47, 4916-4924; Herrera-Alonso et al., Langmuir 2006, 22, 1646-1651) are especially attractive due to the possibilities of reaching a higher ligand density than those based on terminal amino and/or carboxylic groups. Prevention of non-specific interactions of the materials with biomolecules, i.e. establishing biocompatibility, can be improved by immobilization of layers of hydrophilic polymers such as dextran or chitosan (Shi et al., Journal of Chromatography B 2005, 819, 301-306; Xia et al., Journal of Membrane Science 2003, 226, 9-20), or by incorporating polyethylene into the polyamide matrix (Mochizuki et al., Journal of Applied Polymer Sciences 1997, 65, 1713-1721).

Polyamide membranes are made by a dissolution/reprecipitation (wet phase inversion) process and there are several ways to bring about phase separation of a polyamide solution when such membranes are manufactured, normally by a casting or extrusion procedure. One such route is to dissolve the polymer in a single good solvent or a mixture of an intermediate and a good solvent, and then exposing the cast precursor polymer solution to a non-solvent, leading to coagulation. This solvent-induce precipitation can be effectuated either by immersion in a liquid bath or by exposure to saturated vapor of a non-solvent. Other ways of inducing precipitation is through selective evaporation, by selecting a solvent mixture such that the good solvent is the more volatile member of a solvent pair, or by lowering the temperature below the upper critical solution temperature (UCST). Among these techniques, precipitation by treatment with a non-solvent seems to be the most popular. The solvent/non-solvent system employed for solvent-induced precipitation of polyamides 6 and 66 is usually formic acid/water (Shih et al., Journal of Applied Polymer Sciences 2005, 96, 944-960), although in some cases more exotic solvent mixtures such as 2,2,2-trifluoroethanol/compressed $CO_2$ (Kho et al., Polymer 2001, 42, 6119-6127) are used. Films of polymer dope solutions cast on surfaces that do not form adhesive bonds to the polymer can be directly immersed into a non-solvent bath and the polymer precipitates by the exchange of solvents by non-solvents to form porous membranes. Studies of the mechanism of membrane formation has had great impact on the compositions of polymer solutions and non-solvent baths on the membrane morphology (Shih et al., Journal of Applied Polymer Sciences 2005, 96, 944-960; Wienk et al., Journal of Membrane Science 1996, 113, 361-371). The resulting membranes have different morphologies depending on whether a liquid-liquid or a solid-liquid phase separation occurs first.

SUMMARY OF THE INVENTION

It has been found that porous polyamide monoliths can also be prepared using a dissolution/reprecipitation (wet phase inversion) process. Unexpectedly, in spite of the fact that the monoliths are produced in a confined space, the process according to the present invention provides polyamide monoliths with a homogenous pore structure.

The present invention provides a method for producing polyamide monoliths, comprising the steps of
a) providing a polyamide;
b) providing a polyamide-dissolving solvent;
c) adding said polyamide to said polyamide-dissolving solvent;
d) heating the mixture obtained in step c) to a predetermined temperature and incubating said mixture at said predetermined temperature at least until said polyamide has been dissolved in said polyamide-dissolving solvent;
e) cooling said mixture to induce precipitation of said polyamide; and
f) recovering polyamide monoliths from said mixture.

In a preferred embodiment, the method according to the present invention is performed in a confined space so that the confined space is homogenously filled with the polyamide monolith.

More specifically, the present invention provides a method for preparing a capillary monolith, wherein the steps of
i) providing a capillary;
ii) treating the inner surface of the capillary with a silane comprising functional groups capable of covalently binding to the amino or carboxy terminal groups of the polyamide;
are carried out before the above mentioned steps a)-c);
the step of
iii) adding the mixture of polyamide-dissolving solvent and polyamide to said capillary;
is carried out between steps c) and d); followed by
iv) carrying out steps d) and e); and
v) recovering capillaries containing monoliths bound to the capillaries.

Preferably, the polyamide-dissolving solvent is chosen from the group of benzyl alcohol, dimethyl sulfoxide, dichloromethane, trichloromethane, 2,2,2-trifluoroethanol and 1,1,1,2,2,2-hexafluoro-2-propanol. More preferably, the polyamide-dissolving solvent is chosen from the group of benzyl alcohol, dichloromethane, trichloromethane, 2,2,2-trifluoroethanol and 1,1,1,2,2,2-hexafluoro-2-propanol. Most preferred is benzyl alcohol.

Preferably, said predetermined temperature is at least 100° C. Still more preferably, the predetermined temperature is within the range of 130-180° C., and most preferably within the range of 150-160°.

Preferably, said dissolution step d) lasts until the polymer forms a homogenous solution in the chosen solvent at the chosen temperature.

The present invention also provides a polyamide monolith that can be produced by the above disclosed method. In a preferred embodiment the invention provides a capillary containing a polyamide monolith bound to its inner surface that can be produced by the above disclosed method.

DETAILED DESCRIPTION OF THE INVENTION

According to the present invention a monolith is a shaped article which expands in three dimensions. A monolith according to the present invention might be a particle, a column or any other shaped article. In a preferred embodiment, the monoliths according to the present inventions are cylindrical.

The monoliths according to the present invention are produced in a confined space, also called closed vessel or mould. The mould typically defines the future shape of the monolith. For chromatographic purposes, the mould typically is a capillary column or a column with larger dimensions.

Capillary columns according to the invention typically have inner diameters of or below 10 mm, preferably between 100 μm and 2 mm.

The diameter of (bigger) columns used for chromatography can range from 10 mm to several centimeters. For the present invention, the columns typically have inner diameters below 4 cm.

In a preferred embodiment, the shaped articles in which the monoliths are produced are capillary columns with diameters between 100 μm and 10 mm.

The other dimensions and characteristics of the capillary columns and columns resemble those which can be typically found for capillary columns and columns for chromatographic applications.

In the dissolution/reprecipitation (wet phase inversion) process according to the present invention, the change in solubility is established by physical means, i.e. a temperature change. The critical solution temperature for a given polymer is dependent on the solvent composition.

As indicated above, the present method for producing monolithic structures starts with a ready-made polymer and creates the structure by a dissolution/reprecipitation process.

The casting approach, where a surface is open to manipulation, enables modeling of the lateral pore size distribution in thin membranes. This is desirable when a purpose is to make "skin membrane" for ultrafiltration, but would be highly detrimental to a separation column where the flow resistance and hence the pore size distribution should be as even as possible.

It has been found that when performing the precipitation in a closed mould, the precipitation can be effectuated homogenously throughout the entire structure. In a preferred embodiment, the method according to the present invention also involves a mechanism that ascertains attachment of the precipitated polymer to the wall of the mould.

The polyamides that can be used according to the present invention are linear aliphatic polyamides. Examples are PA 69 (CAS 28757-63-3) from EGA Chemie (Steinheim, DE), PA 46 (CAS 50327-22-5), PA 610 (CAS 9008-66-6) from Aldrich (Schnelldorf, DE), PA 6 (CAS 25038-54-4, Ultramid B27 E, Mn 18,000), PA 66 (CAS 32131-17-2, Ultramid A27 E 01, Mn 18,000) and PA 6/66 (CAS 24993-04-2, Ultramid C31 01, Mn 24,000) as well as Spin Abulon 0.70 mm (ABU Garcia, Marignier, FR). The polyamides can be used as single compound or as mixtures of two or more different polyamides. In the following, the term "polyamide" stands for a single polyamide or mixtures of two or more different polyamides.

As polyamide-dissolving solvent any solvent can be used in which polyamides can be dissolved and reprecipitated depending on the temperature. Preferably, the polyamide-dissolving solvent is chosen from the group of benzyl alcohol, dimethyl sulfoxide, dichloromethane, trichloromethane, 2,2,2-trifluoroethanol and 1,1,1,2,2,2-hexafluoro-2-propanol. The polyamide-dissolving solvent can be a single solvent or a mixture of one or more solvents. More preferably, the polyamide-dissolving solvent is benzyl alcohol.

For performing the method according to the present invention, the polyamide is dissolved in a polyamide-dissolving solvent at elevated temperature. Preferably, said predetermined temperature is at least 100° C. Still more preferably, the predetermined temperature is within the range of 130-180° C., and most preferably within the range of 150-160° C.

The mixture is then incubated at said predetermined elevated temperature at least until said polyamide has been dissolved in the polyamide-dissolving solvent. The incubation time typically varies between one hour and several days.

A suitable percentage of polyamide in the mixture is between 5 and 50% (w/w) polyamide, preferably between 10 and 30%.

Afterwards, the mixture is cooled until the polyamide reprecipitates. The cooling can for example be performed rapidly by applying cooling aids or slowly by just removing or lowering the heating. A person skilled in the art is able to adjust the cooling process to his needs. Apart from the percentage of polyamide in the mixture, the cooling rate is a good means to influence the structure—especially the pore structure—of the resulting monolith. The mixture is typically cooled down to room temperature.

The resulting polyamide monoliths are typically macroporous with a continuous and evenly spaced macropore system.

The method according to the present invention is typically performed in a mould which defines the future size of the polyamide monolith. The mould can be any shaped article, for example is can be a box or tube. In a preferred embodiment, it is a capillary column. The mould can be made of any material which is stable under the preparation conditions of the monolith. In a preferred embodiment, the mould is made of an inert plastics, metal or glass. In a very preferred embodiment, the mould is a fused silica capillary. To ensure a tight connection between the polyamide monolith and the mould preferably comprises at its inner surface functional groups capable of covalently binding to the amino or carboxy terminal groups of the polyamide. To achieve this, it can for example be pre-treated with a silane comprising functional groups capable of covalently binding to the amino or carboxy terminal groups of the polyamide. Suitable silanes are for example 3-glycidoxypropyl-trimethoxysilane (GLYMO), 3-glycidoxypropylmethyldimethoxysilane, 3-glycidoxypropylmethyldiethoxysilane, 3-aminopropylmethyldiethoxysilane, 3-aminopropyldimethylethoxysilane, 3-aminopropyltriethoxysilane or 3-aminopropyltrimethoxysilane.

It has been found that it is also possible to produce the polyamide monolith in columns which are already filled with a skeleton or macroporous structures of other materials like for example silica. For this application, the polyamide is dissolved in an appropriate solvent at appropriate temperature and then filled in the column. When cooling the mixture, the polyamide monolithic structures form in the pores of the silica structures.

In one embodiment of the present invention, one can also add other compounds to the mixture of the polyamide and the solvent. This can be particles, template molecules, molecules of particles with certain functionalities or reactive groups. When the polyamide reprecipitates, these compounds are integrated into the monolithic structure.

The polyamide monoliths according to the present invention can be used as such or can be further modified. If the materials according to the present invention are used as sorbents for chromatographic separations, they are usually derivatized in order to allow different mechanisms of separations. Methods for such derivatizations and the use of such derivatized separating materials are known in the art. The groups which are introduced into the polyamide base material in order to allow chromatographic separations can be summarized as separation effectors. Examples for different modes of chromatographic separations are ion exchange chromatography, reversed phase chromatography, hydrophobic interaction chromatography, affinity chromatography, chiral separations. Dependent on these modes of action different separation effectors can be used. Examples are ionic groups like —COON, —$SO_3H$, —$N(C_2H_5)_2$, or —$N^+(C_2H_5)_3$, hydrophobic groups like $C_{18}$- or $C_8$-alkyl or phenyl or butyl, affinity ligands like antibodies or enzyme substrates (or substrate analogues), chiral ligands like aminoacid derivatives or polysaccharide derivatives.

Without further elaboration, it is believed that one skilled in the art can, using the preceding description, utilize the present invention to its fullest extent. The preferred specific embodiments are, therefore, to construed as merely illustrative, and not limitative of the disclosure in any way whatsoever.

The entire disclosures of all applications, patents, and publications cited above and below, and of corresponding applications SE 0800375.8 and U.S. 61/029,582 filed Feb. 19, 2008 are hereby incorporated by reference.

BRIEF DESCRIPTION OF THE FIGURES AND TABLES

Figure 2:
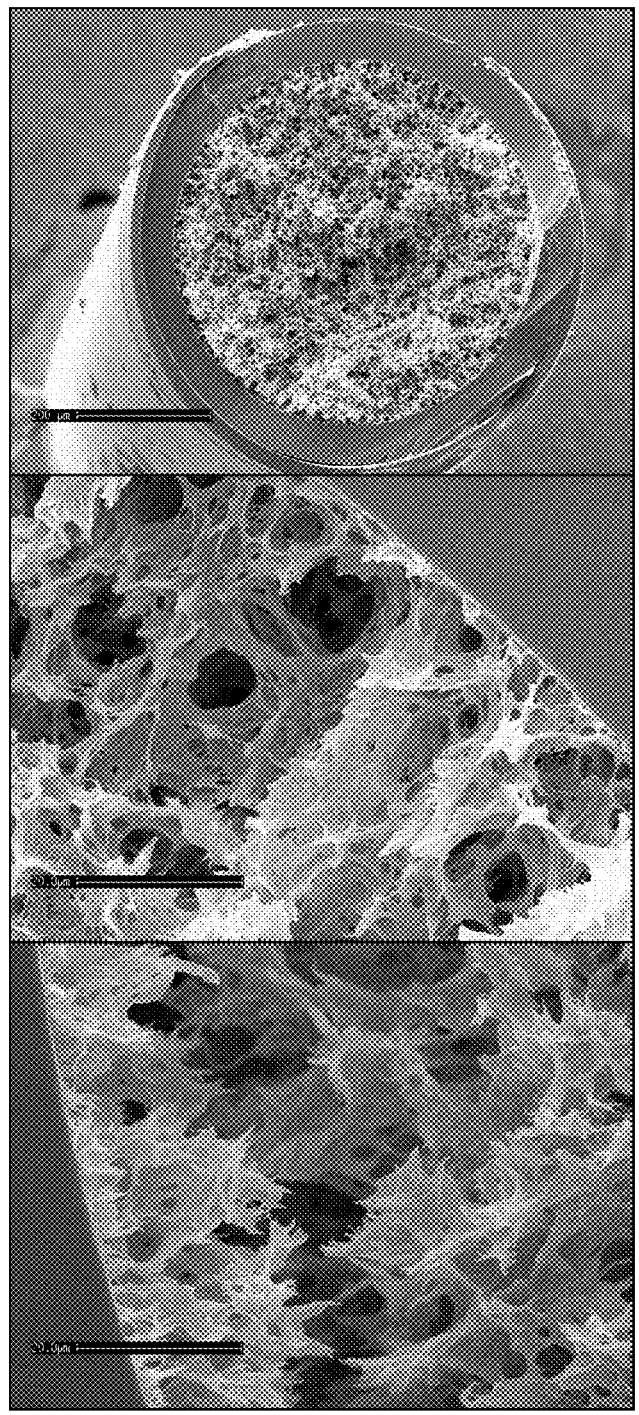
Figure 3:
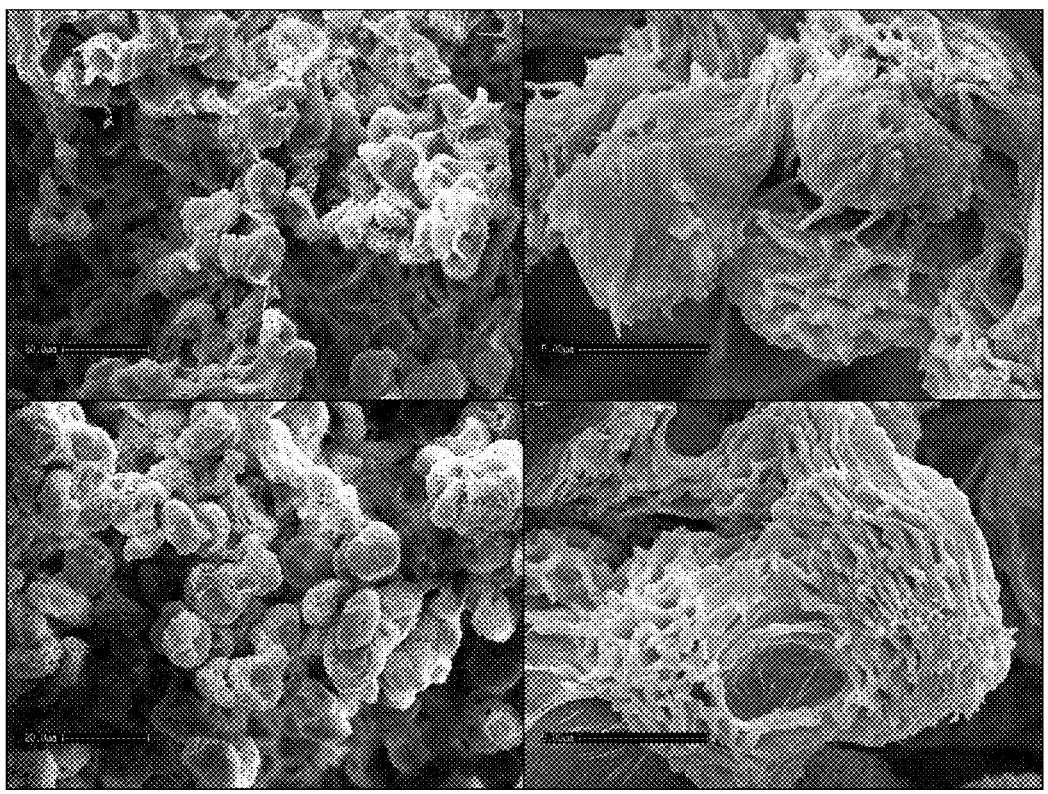
Figure 4:
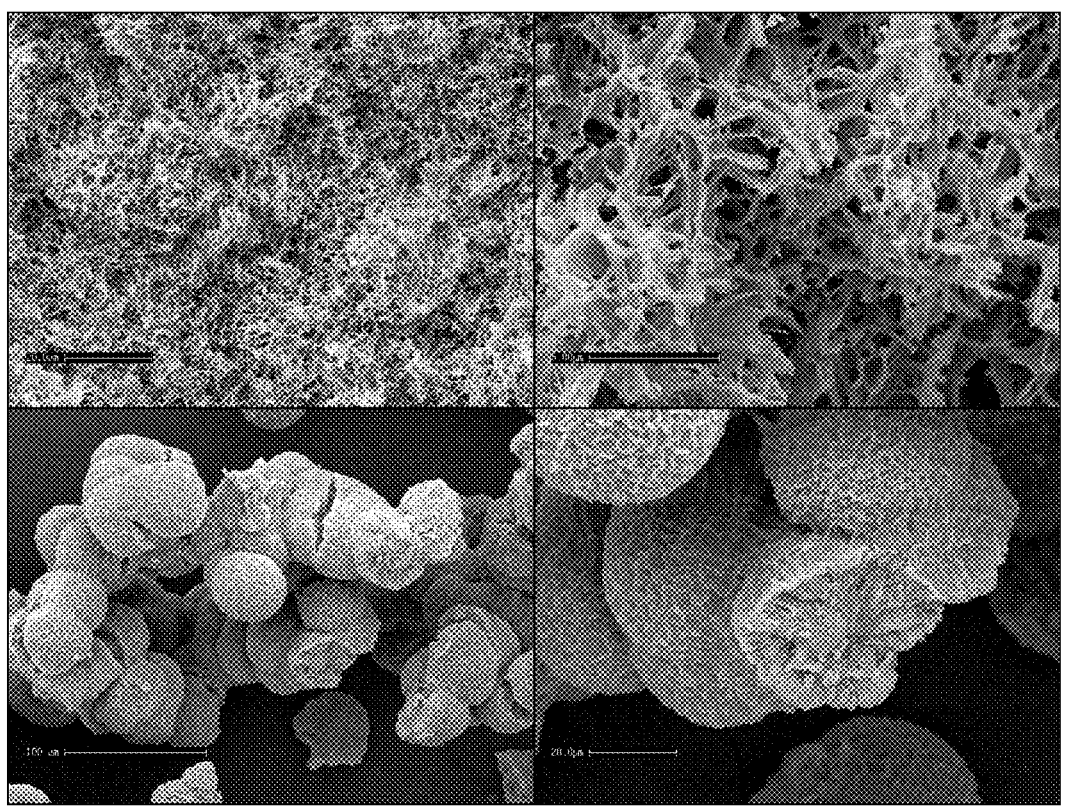
Figure 5:
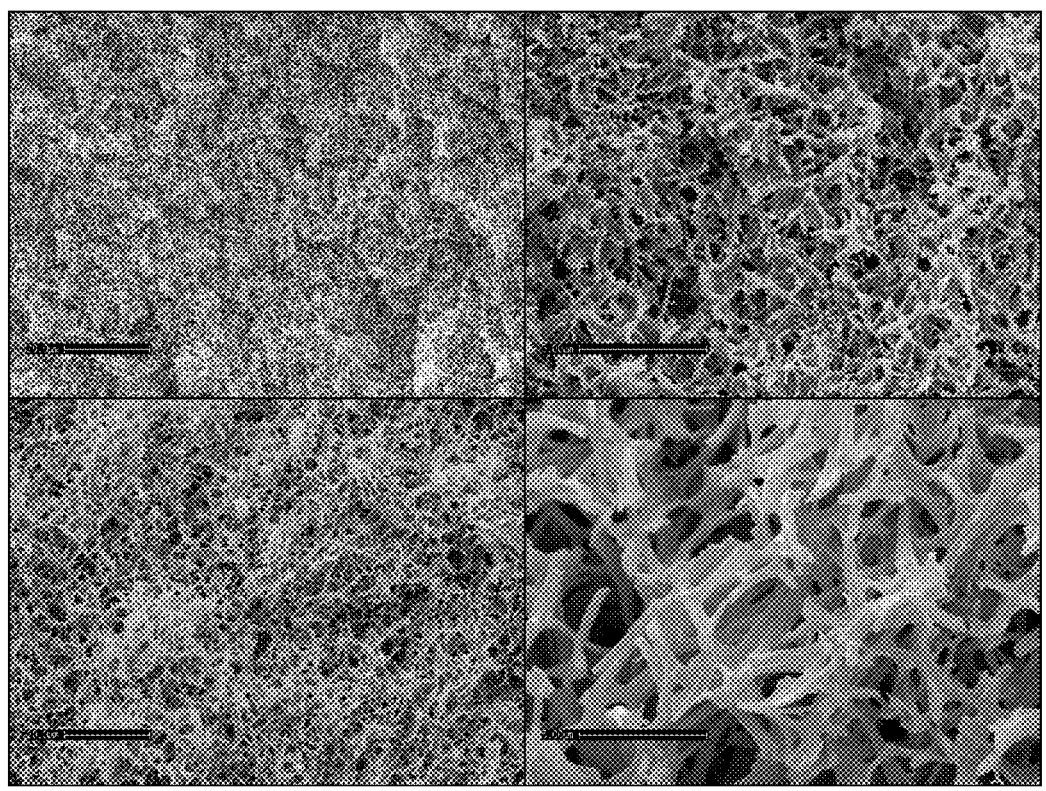
Figure 6:
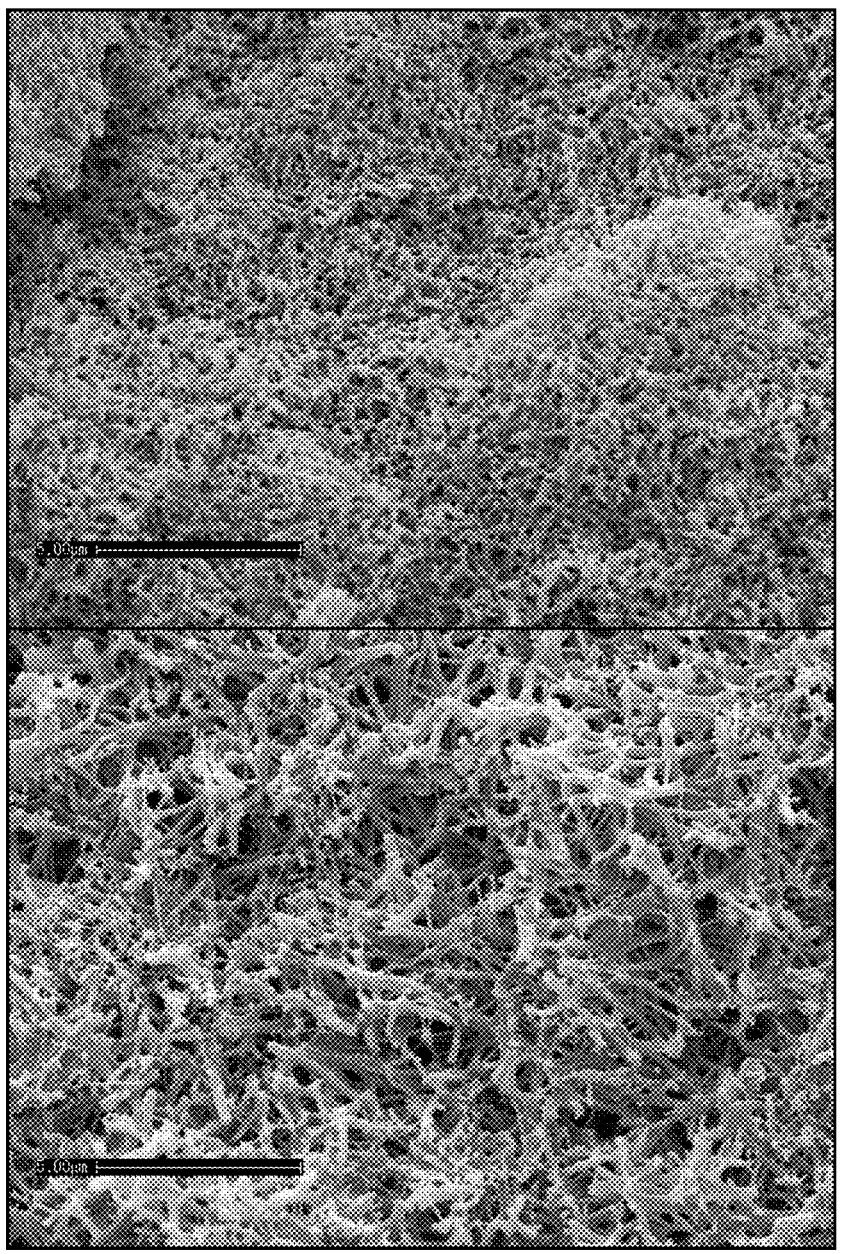

The present invention will now be described with reference to the enclosed figures and tables, in which:

FIG. 1 shows a temperature profile of the cooling process of the polyamide solutions prepared in vials with a fitted exponential trendline;

FIG. 2 discloses scanning electron micrographs of a monolith prepared from a chopped fishing line in a capillary column. The material was dissolved, precipitated by fast cooling to room temperature followed by subsequent evaporation of the solvent by vacuum. a) Cross-section of the entire capillary, showing a homogenous structure across the diameter; b) Close-up showing the attachment to the fused silica surface; c) fracture surface showing that the adhesive properties are stronger than the cohesive properties of the monolithic structure;

FIG. 3 presents scanning electron micrographs showing the morphologies of macroporous PA6/66 monoliths with 12% (w/w) polymer loading made by dissolution at 140-150° C. for 4 hours (a and b) and 48 hours (c and d) followed by slow cooling to room temperature. Each material is shown at two different magnifications, as indicated in the SEMs;

FIG. 4 reveals scanning electron micrographs showing the morphologies of macroporous PA 610 monoliths with 12% (w/w) polymer loading made by dissolution at 140-150° C. for four hours (a and b) and 48 hours (c and d) followed by slow cooling to room temperature. The monoliths prepared by the longer dissolution time showed extensive cracking and disintegrated on drying, hence the detached fragment shown in c). Each material is shown at two different magnifications, as indicated in the SEMs;

FIG. 5 shows macroporous materials made from PA6 (12% w/w) with the intended dissolution times at different magnifications;

FIG. 6 shows macroporous materials made from PA6 (19% w/w) with the intended dissolution times at different magnifications; and Table 1 discloses surface areas and average mesopore and flowthrough pore diameter determined by nitrogen gas adsorption technique where BET and BJH methods were used to estimate the surface areas and mesopore diameter, respectively. These monoliths were prepared by dissolving PA6 (19% polymer loading) in benzyl alcohol for 2.5H and 5.5 h.

TABLE 1

| Dissolution time (h) | Surface area (m²/g) | Average mesopore diameter (Å) |
|---|---|---|
| 2.5 | 52.2 | 147.2 |
| 5.5 | 49.0 | 142.9 |

Experimental Part

The present invention will now be described with reference to the following examples. These examples are provided for information purposes and should not be interpreted as restricting the scope of the present invention.

Reagents and Materials

The polyamides were PA 69 (CAS 28757-63-3) from EGA Chemie (Steinheim, DE), PA 46 (CAS 50327-22-5), and PA 610 (CAS 9008-66-6) from Aldrich (Schnelldorf, DE). PA 6 (CAS 25038-54-4, Ultramid B27 E, Mn 18,000), PA 66 (CAS 32131-17-2, Ultramid A27 E 01, Mn 18,000) and PA 6/66 (CAS 24993-04-2, Ultramid C31 01, Mn 24,000) were gifts from BASF (Ludwigshafen, DE). The very first experiments were carried out using Spin Abulon 0.70 mm (ABU Garcia, Marignier, FR) monofilament fishing line (composition unknown) as polyamide source. The benzyl alcohol (p.a.) was from Merck (Darmstadt, DE) and the methanol used for flushing the benzyl alcohol out of the materials was of "pure grade" from Prolabo (Paris, FR). Dried toluene from Fischer (Fairlawn, N.J., US) was used as solvent for 3-glycidoxypropyl trimethoxysilane (Aldrich) in surface modification of inner walls of 530 μm i.d. polyimid-coated fused silica capillaries, obtained from Polymicro Technologies (Phoenix, Ariz., US).

Example 1

Bulk Monolith Preparation

Polyamide solutions were prepared by dissolving ~120-190 mg of each polyamide in 1 g benzyl alcohol. The dissolution took place in 1.5 ml borosilicate vials sealed with PTFE-faced septa and crimp caps for varying periods of time. During the dissolution, the vials were immersed in a sand bath that was placed in a convective laboratory oven (Electrolux, SE), where the temperature measured over time and at different spots in the sand bath varied from 150-160°. This temperature variation was mainly due to frequent opening of the oven to carry out the mixing cycles, which consisted of a gentle manual shake for 5-10 s every 30 min in order to facilitate the dissolution of the swollen polymer. After 4-5 shaking cycles the solutions appeared homogenous and were then left unstirred in the sand bath for up to 48 h to ascertain complete dissolution. The solutions were then allowed to cool slowly to room temperature by turning off the oven with the vials still submerged in the sand bath. The temperature profile of the cooling process is shown in FIG. 1. A week after the dissolution the vials were carefully broken to recover the resulting gels as intact as possible. These gels were then subjected to Soxhlet extraction with methanol to remove the solvent and then left to dry in air before the SEM images were taken. Prior to surface area and pore size determinations, further drying was made by dividing the monolith into cubes with sides of 2-3 mm that were purged by dry nitrogen at 50° C. for 2-3 h.

Example 2

Capillary Monolith Preparation

Method:

For the capillary column format, the capillaries were pretreated, firstly by etching with 1 M aqueous NaOH for 2 h, then thoroughly washed in sequence with water and dried acetone, and finally dried with nitrogen gas. The dry activated capillaries were then reacted with 3-glycidoxypropyl trimethoxy silane in dried toluene (1:4 v/v) at 110° C. for 6 h, with following toluene and acetone washing steps. The polyamide solutions for the capillary experiments were prepared in the same way as above, with a total heating time of about 3 h. Directly upon removal from the oven and while still in the sand bath, the polymer solutions were flushed from the glass vials into the capillaries by piercing the septum with a piece of unheated capillary and compressed helium supplied through a hypodermic needle was used to propel several capillary volumes of the solution from the vial into the capillary, at a rate fast enough to heat the capillary during this process. The filled capillaries were rapidly wiped off and sealed by pieces of rubber septum and then immediately placed in the oven where they remained at the dissolution temperature for 2 h, to accelerate the reaction between terminal amino groups of polyamide chains and the oxiranes on the capillary inner surfaces. After this attachment step, the capillaries were quickly cooled to room temperature and a week later placed in a vacuum chamber at a partial vacuum (~1 kPa) for ~4 weeks to evaporate the solvent at room temperature. The residual solvent remaining after the vacuum removal step was washed out by flushing MeOH through the columns.

In a specific experiment, the precipitation took place in polyimide-coated fused silica capillaries with 530 μm i.d. (polymicro Technologies, Phoenix, Ariz., US) to ascertain a fast thermal transfer. Capillaries (~10 cm) treated with 3-glycidoxypropyl-trimethoxysilane (GLYMO) for immobilization of the polyamide through the amino terminal, were filled with the hot polyamide solution by piercing the capillary through the vial septum and applying nitrogen gas pressure to the vial through a hypodermic syringe to ensure rapid filling. A sufficient excess of hot solution was flushed to ensure that the temperature in the capillary was above UCST before the capillary ends were closed by pieces of silicone rubber septa. The filled capillary was thereafter heated for 2 hours at the dissolution temperature before cooling was initiated. The benzyl alcohol was removed from the capillaries by applying partial vacuum (~100 Pa) with both ends open during a period of 4 weeks. The capillaries were then flushed with methanol.

Comments:

Since the porous structure was to be formed in a closed vessel and attachment to the wall is required for flow applications, the preliminary investigations were aimed at finding conditions for securing attachment of the polyamide monolith to the fused silica capillary. The conditions for attachment of vinylic monoliths to fused silica surfaces through silylation with 3-methacryloyloxypropyl trimethoxysilane (γ-MAPS) have previously been investigated, and hence it was attempted to use one of the silylation schemes that worked best also for this purpose. However, the functionality of the silyl anchoring group would have to be different and it was decided to test corresponding oxirane reagent, 3-glycidopropyl trimethoxysilane (GLYMO) with a similar etching scheme and a more forceful silylation step, which is possible as GLYMO is not subject to the same risk for spontaneous polymerization as γ-MAPS. The intention was to attach PA to the wall through the terminal amino groups by condensation with the oxirane and hence secure that the monoliths were firmly attached to the wall by incorporation of the tethered PA chains with the precipitated structure. In those exploratory experiments chopped-up pieces of monofilament fishing line as polyamide source, and the first results obtained were indeed encouraging. Not only was a monolithic structure with micron-sized pores of homogenous density across the capillary formed (FIG. 2a); the chopped fishing line monolith also appeared so securely attached to the capillary wall that the adhesive forces exceeded the cohesive forces in the nylon monolith (FIG. 2b). As is seen in the close-up FIG. 2c, the compatibility of the polymer with the polyamide-modified silica surface seems very good as the attachment points spread on the surface. None of the SEMs of snapped capillaries showed polyamide being detached from the silica surface by peeling. Instead, the fractures were always found in the monolith structure itself. It was therefore concluded that the chosen etching and activating procedure was well suited for this purpose.

Example 3

Surface Area Determination

The specific surface area was determined by nitrogen adsorption-desorption on a Micrometrics (Norcross, Ga., US) Tristar 3000 automated gas adsorption analyzer, measuring multipoint surface area and average pore width of the particles based on the Brunauer-Emmett-Teller equation (Brunauer, S., *The Adsorption of Gases and Vapors. I. Physical Adsorption.*, Princeton University Press, Princeton, 1945). The Tristar 3000 was also used to calculate the total pore volume of the particles by measuring $N_2$ adsorption close to atmospheric pressure. Before analysis the monolithic cubes were dried in a vacuum oven at 40° C. overnight to remove adsorbed gases from the pores. Approximately 100 mg of material was placed in a sample tube and dried again before analysis at 120° C. for at least 3 hours under continuous nitrogen flow, using a Micrometrics SmartPrep degassing unit. Results can be found in table 1. It was found that the materials with more or less rod-type morphologies (PA6) had higher specific surface areas than those with coral-like clusters in the structures (PA6/66). In case of PA6, longer time of dissolution gave rise to larger flow-through pores but smaller surface areas.

Example 4

Mercury Intrusion Porosiometry

Pore size estimation was carried out on a Micrometrics AutoPore IV 9500 mercury intrusion porosimeter capable of generating pressure up to 425 MPa, corresponding to a minimal cylindrical pore diameter of 3 nm. The mercury contact angle was set to 130°, intrusion/extrusion was then performed up to 17.23 MPa by small pressure increments, yielding a total of 171 points. A blank correction file was used to compensate for compressibility of mercury and penetrometer parts. Data acquisition and calculation of results were done using the AutoPore IV 9500 software, version 1.07. Results can be found in table 1. FIG. 5 shows a rather narrow distribution of convective poresize between 1-2.2 µm of the pore diameter area.

Example 5

Scanning Electron Microscopy

Some samples for scanning electron microscopy (SEM) were prepared by freezing the structures in liquid nitrogen and crushing the pieces or snapping the fused silica capillaries to obtain freeze fracture surfaces. Before the actual electron microscopy procedure, all samples were placed on sticky carbon foils (used to increase conductivity) attached to standard aluminum specimen stubs and coated with ~20 nm of gold by using a combination of sputter coating by an Edwards (Crawley, GB) model 5150A sputter coating unit, and evaporation by a modified Edwards E14 vacuum coating unit, incorporating an automatic tilting and rotation device. Microscopic analysis of all samples was carried out in an S-360 iXP SEM (Leica Cambridge Ltd., Cambridge, GB) operated at 10 kV, 100 pA probe current, and 0° tilt angle. Final images were recorded from randomly chosen areas at a magnification indicated in each SEM.

Example 6

Choice of Solvents

The polyamides were dissolved in a non-acidic solvent at elevated temperature. The solutions were cooled to room temperature to precipitate the polymer and afterward the solvent were removed from the resulting gels by Soxhlet extraction or vacuum. The period of time of dissolution of the polyamide in benzyl alcohol and cooling conditions had significant impacts on the morphology and the mechanical properties of the final materials. The possibility of grafting the materials onto the glass wall make it more attractive to liquid chromatography applications.

Numerous non-acidic solvents or solvent mixtures have been described in the literature for dissolution of linear aliphatic polyamides (Robert et al., *Pure Appl. Chem.* 2004, 76, 2009-2025; Steadman et al., *Polymer* 1996, 38, 5297-5300; Kartalis et al., *Journal of Applied Polymer Sciences* 2002, 86, 1924-1930). Among these are dimethylsulfoxide, dichloromethane, trichloromethane, 2,2,2-trifluoroethanol, 1,1,1,3,3,3-hexafluoro-2-propanol, and benzyl alcohol. The choice fell on benzyl alcohol as it is one of relatively few solvents capable of dissolving polyamides that requires elevated temperatures to work; in other words were several polyamides show the required LCST behaviour. The initial conditions were chosen based on the work of Robert et al., (Robert et al., *Pure Appl. Chem.* 2004, 76, 2009-2025), who investigated conditions for dissolution of polyamides for size exclusion chromatography in various solvents, and the temperature and time chosen immediately yielded satisfactory results. Due to its relatively low toxicity, benzyl alcohol was therefore preferred for the continued dissolution/reprecipitation experiments of the aliphatic polyamides.

A drawback with benzyl alcohol was that among the polyamides tested, it could only dissolve PA 6, PA6/66 and PA 610 completely under the experimental conditions in spite of the dissolution being prolonged for up to 7 days. Copolymer PA 6/66 required the shortest time (less than 45 min) for the solution to appear clear, while PA 6 took the longest time (~4 h), which can be attributed to the regularity and density of the interchain hydrogen bonds in PA 6. The morphologies of the final materials are presented in FIGS. 3, 4 and 5, for dissolution times of 4 and 48 h. There are clearly differences in the structures produced, both between the different polymers and for different dissolution times. PA 6/66 gave at both dissolutions times quite similar coral-like connected clusters (FIG. 3), which were not the three-dimensional skeleton type structures which the present investigation aimed at finding. Such structures were observed for the lower dissolution time with PA610 (FIGS. 4a and 4b), but when the dissolution was extended to 48 h, even more pronounced coral-like structures were produced (FIGS. 4c and 4d). With PA 6, skeleton structures of the connected rod type were produced at both dissolution times (FIG. 5), but the feature size of the skeletons was substantially larger for the monolith prepared from the precursor solution with the longer dissolution time (FIGS. 5c and 5d). In the bulk materials we also noted that monoliths prepared by dissolution for 4 h shrunk considerably more than the ones produced with the longer dissolution time. It was further found that all monoliths produced from polyamides that were kept at the dissolution temperature for 48 h turned out to be more brittle than the counterparts dissolved for only 4 h. The PA 610 was an extreme in this respect and the monolithic material produced from the solution with longer dissolution time disintegrated into small pieces upon drying. The monoliths prepared from PA 6 were strong and sufficiently elastic to be cut by a scalpel without cracking apart for the lower dissolution.

Example 7

The Effect of the Cooling Process on the Structure of the Monoliths

An abrupt decrease in temperature of the cooling process produced larger and unevenly distributed pore sizes while a slow decrease in temperature gave rise to the formation of 3D-skeleton structure.

The invention claimed is:

1. A method for producing polyamide monoliths, comprising, in a confined space,
   a) providing a polyamide;
   b) providing a polyamide-dissolving solvent;
   c) adding said polyamide to said polyamide-dissolving solvent;
   d) heating the mixture obtained in c) to a predetermined temperature and incubating said mixture at said predetermined temperature at least until said polyamide has been dissolved in said polyamide-dissolving solvent;
   e) cooling said mixture; and
   f) recovering polyamide monoliths from said mixture.

2. A method according to claim 1, wherein the polyamide monoliths are produced in a capillary column.

3. A capillary comprising a polyamide monolith bound to its inner surface produced by the method according to claim 2.

4. A method for the chromatographic separation of at least two substances, said method comprising subjecting a sample containing said at least two substances to chromatographic separation in a capillary according to claim 3.

5. A method according to claim 2, wherein the inner surface of the capillary has been treated with a silane comprising functional groups capable of covalently binding to the amino or carboxy terminal groups of the polyamide.

6. A method according to claim 1, wherein the polyamide-dissolving solvent is benzyl alcohol, dimethyl sulfoxide, dichloromethane, trichloromethane, 2,2,2-trifluoroethanol or 1,1,1,2,2,2-hexafluoro-2-propanol.

7. A method according to claim 1, wherein the polyamide-dissolving solvent is benzyl alcohol.

8. A method according to claim 1 wherein said predetermined temperature is at least 100° C.

9. A method according to claim 1, wherein dissolution d) lasts until the polymer forms a homogenous solution in the chosen solvent at the chosen temperature.

10. A polyamide monolith produced by the method according to claim 1.

11. A method according to claim 1 wherein said predetermined temperature is 130-180° C.

12. A method according to claim 1 wherein said predetermined temperature is 150-160° C.

13. A method for producing polyamide monoliths, comprising, in a confined space, cooling a dissolved mixture of polyamide and polyamide-dissolving solvent to precipitate said monoliths.

* * * * *

UNITED STATES PATENT AND TRADEMARK OFFICE
CERTIFICATE OF CORRECTION

PATENT NO.       : 8,535,527 B2                                           Page 1 of 1
APPLICATION NO.  : 12/918173
DATED            : September 17, 2013
INVENTOR(S)      : Knut Irgum It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 349 days.

Signed and Sealed this

Fifteenth Day of September, 2015

Michelle K. Lee
*Director of the United States Patent and Trademark Office*